(12) United States Patent
Clawson

(10) Patent No.: US 8,294,570 B2
(45) Date of Patent: Oct. 23, 2012

(54) BURN DIAGNOSTIC AND INTERVENTION TOOL FOR EMERGENCY DISPATCH

(76) Inventor: Jeffrey J. Clawson, Salt Lake City, UT (US)

( * ) Notice: Subject to any disclaimer, the term of this patent is extended or adjusted under 35 U.S.C. 154(b) by 500 days.

(21) Appl. No.: 12/712,017

(22) Filed: Feb. 24, 2010

(65) Prior Publication Data

US 2011/0205052 A1 Aug. 25, 2011

(51) Int. Cl.
*G08B 1/08* (2006.01)
*G08B 23/00* (2006.01)
*A61B 5/00* (2006.01)
*G06F 3/00* (2006.01)

(52) U.S. Cl. ............ 340/539.12; 340/539.1; 340/573.1; 600/300; 715/700; 715/733; 715/741; 715/744; 715/764; 715/765

(58) Field of Classification Search .................. None
See application file for complete search history.

(56) References Cited

U.S. PATENT DOCUMENTS

| | | |
|---|---|---|
| 3,799,147 A | 3/1974 | Adolph et al. |
| 4,130,881 A | 12/1978 | Haessler et al. |
| 4,164,320 A | 8/1979 | Irazoqui et al. |
| 4,237,344 A | 12/1980 | Moore |
| 4,290,114 A | 9/1981 | Sinay |
| 4,338,493 A | 7/1982 | Stenhuis et al. |
| 4,360,345 A | 11/1982 | Hon |
| 4,455,548 A | 6/1984 | Burnett |
| 4,489,387 A | 12/1984 | Lamb et al. |
| 4,731,725 A | 3/1988 | Suto et al. |
| 4,839,822 A | 6/1989 | Dormond et al. |
| 4,858,121 A | 8/1989 | Barber et al. |
| 4,865,549 A | 9/1989 | Sonsteby |
| 4,922,514 A | 5/1990 | Bergeron et al. |
| 4,926,495 A | 5/1990 | Comroe et al. |
| 4,945,476 A | 7/1990 | Bodick et al. |
| 4,967,754 A | 11/1990 | Rossi |
| 5,063,522 A | 11/1991 | Winters |
| 5,065,315 A | 11/1991 | Garcia |

(Continued)

FOREIGN PATENT DOCUMENTS

JP 2003109162 A 4/2003

(Continued)

OTHER PUBLICATIONS

International Preliminary Report of Patentability for PCT/US2009/048577 filed on Jun. 25, 2009 mailed Oct. 27, 2011, 7 pgs.

(Continued)

*Primary Examiner* — Julie Lieu
(74) *Attorney, Agent, or Firm* — John R. Thompson; Stoel Rives LLP

(57) ABSTRACT

A system and method to assist an emergency medical dispatcher in responding to emergency calls is disclosed. A computer-implemented emergency dispatch protocol is provided that includes interrogatories for a dispatcher to ask a caller to generate an appropriate response. A diagnostic tool is provided to aid a dispatcher in calculating a burn surface area of a patient. The diagnostic tool calculates the burn surface area based on caller relayed information about the areas of the patient's body that are burned. The burn calculation may be based on the Rule of Nines methodology. The diagnostic tool can be launched automatically by the emergency dispatch protocol, or manually as desired by a dispatcher. The diagnostic tool presents a user interface that may provide, among other things, instructions, a visual portrayal of the human body, and input fields.

31 Claims, 8 Drawing Sheets

U.S. PATENT DOCUMENTS

| | | | |
|---|---|---|---|
| 5,072,383 A | 12/1991 | Brimm et al. |
| 5,077,666 A | 12/1991 | Brimm et al. |
| 5,086,391 A | 2/1992 | Chambers |
| 5,109,399 A | 4/1992 | Thompson |
| 5,122,959 A | 6/1992 | Nathanson et al. |
| 5,193,855 A | 3/1993 | Shamos |
| 5,228,449 A | 7/1993 | Christ et al. |
| 5,253,164 A | 10/1993 | Holloway et al. |
| 5,255,187 A | 10/1993 | Sorensen |
| 5,291,399 A | 3/1994 | Chaco |
| 5,323,444 A | 6/1994 | Ertz et al. |
| 5,339,351 A | 8/1994 | Hoskinson et al. |
| 5,348,008 A | 9/1994 | Bornn et al. |
| 5,379,337 A | 1/1995 | Castillo et al. |
| 5,404,292 A | 4/1995 | Hendrickson |
| 5,410,471 A | 4/1995 | Alyfuku et al. |
| 5,423,061 A | 6/1995 | Fumarolo et al. |
| 5,438,996 A | 8/1995 | Kemper et al. |
| 5,441,047 A | 8/1995 | David et al. |
| 5,462,051 A | 10/1995 | Oka et al. |
| 5,471,382 A | 11/1995 | Tallman et al. |
| 5,502,726 A | 3/1996 | Fischer |
| 5,513,993 A | 5/1996 | Lindley et al. |
| 5,516,702 A | 5/1996 | Senyei et al. |
| 5,521,812 A | 5/1996 | Feder et al. |
| 5,536,084 A | 7/1996 | Curtis et al. |
| 5,544,649 A | 8/1996 | David et al. |
| 5,554,031 A | 9/1996 | Moir et al. |
| 5,590,269 A | 12/1996 | Kruse et al. |
| 5,594,638 A | 1/1997 | Iliff |
| 5,594,786 A | 1/1997 | Chaco et al. |
| 5,596,994 A | 1/1997 | Bro |
| 5,630,125 A | 5/1997 | Zellweger |
| 5,636,873 A | 6/1997 | Sonsteby |
| 5,650,995 A | 7/1997 | Kent |
| 5,660,176 A | 8/1997 | Iliff |
| 5,675,372 A | 10/1997 | Aguayo, Jr. et al. |
| 5,682,419 A | 10/1997 | Grube et al. |
| 5,684,860 A | 11/1997 | Milani et al. |
| 5,689,229 A | 11/1997 | Chaco et al. |
| 5,719,918 A | 2/1998 | Serbetciouglu et al. |
| 5,722,418 A | 3/1998 | Bro |
| 5,724,983 A | 3/1998 | Selker et al. |
| 5,734,706 A | 3/1998 | Windsor et al. |
| 5,745,532 A | 4/1998 | Campana, Jr. |
| 5,748,907 A | 5/1998 | Crane |
| 5,754,960 A | 5/1998 | Downs et al. |
| 5,759,044 A | 6/1998 | Redmond |
| 5,761,278 A | 6/1998 | Pickett et al. |
| 5,761,493 A | 6/1998 | Blakeley et al. |
| 5,787,429 A | 7/1998 | Nikolin, Jr. |
| 5,805,670 A | 9/1998 | Pons et al. |
| 5,809,493 A | 9/1998 | Ahamed et al. |
| 5,822,544 A | 10/1998 | Chaco et al. |
| 5,823,948 A | 10/1998 | Ross, Jr. et al. |
| 5,826,077 A | 10/1998 | Blakeley et al. |
| 5,832,187 A | 11/1998 | Pedersen et al. |
| 5,842,173 A | 11/1998 | Strum et al. |
| 5,844,817 A | 12/1998 | Lobley et al. |
| 5,850,611 A | 12/1998 | Krebs |
| 5,857,966 A | 1/1999 | Clawson |
| 5,901,214 A | 5/1999 | Shaffer et al. |
| 5,902,234 A | 5/1999 | Webb |
| 5,910,987 A | 6/1999 | Ginter et al. |
| 5,912,818 A | 6/1999 | McGrady et al. |
| 5,915,019 A | 6/1999 | Ginter et al. |
| 5,926,526 A | 7/1999 | Rapaport et al. |
| 5,933,780 A | 8/1999 | Connor et al. |
| 5,961,446 A | 10/1999 | Beller et al. |
| 5,962,891 A | 10/1999 | Arai |
| 5,964,700 A | 10/1999 | Tallman et al. |
| 5,986,543 A | 11/1999 | Johnson |
| 5,989,187 A | 11/1999 | Clawson |
| 5,991,730 A | 11/1999 | Lubin et al. |
| 5,991,751 A | 11/1999 | Rivette et al. |
| 6,004,266 A | 12/1999 | Clawson |
| 6,010,451 A | 1/2000 | Clawson |
| 6,022,315 A | 2/2000 | Iliff |
| 6,035,187 A | 3/2000 | Franza |
| 6,040,770 A | 3/2000 | Britton |
| 6,052,574 A | 4/2000 | Smith, Jr. |
| 6,053,864 A | 4/2000 | Clawson |
| 6,058,179 A | 5/2000 | Shaffer et al. |
| 6,074,345 A | 6/2000 | van Oostrom et al. |
| 6,076,065 A | 6/2000 | Clawson |
| 6,078,894 A | 6/2000 | Clawson et al. |
| 6,106,459 A | 8/2000 | Clawson |
| 6,112,083 A | 8/2000 | Sweet et al. |
| 6,115,646 A | 9/2000 | Fiszman et al. |
| 6,117,073 A | 9/2000 | Jones et al. |
| 6,118,866 A | 9/2000 | Shtivelman |
| 6,127,975 A | 10/2000 | Maloney |
| 6,134,105 A | 10/2000 | Lueker |
| 6,292,542 B1 | 9/2001 | Bilder |
| 6,370,234 B1 | 4/2002 | Kroll |
| 6,535,121 B2 | 3/2003 | Matheny |
| 6,594,634 B1 | 7/2003 | Hampton et al. |
| 6,607,481 B1 | 8/2003 | Clawson |
| 6,610,012 B2 | 8/2003 | Mault |
| 6,696,956 B1 | 2/2004 | Uchida et al. |
| 6,879,819 B2 | 4/2005 | Brooks |
| 6,901,397 B1 | 5/2005 | Moldenhauer et al. |
| 6,931,112 B1 | 8/2005 | McFarland et al. |
| 6,968,375 B1 | 11/2005 | Brown |
| 7,106,835 B2 | 9/2006 | Saalsaa |
| 7,194,395 B2 | 3/2007 | Genovese |
| 7,289,944 B1 | 10/2007 | Genovese |
| 7,428,301 B1 | 9/2008 | Clawson |
| 7,436,937 B2 | 10/2008 | Clawson |
| 7,645,234 B2 | 1/2010 | Clawson |
| 7,703,020 B2 * | 4/2010 | Bhattaru ................ 715/740 |
| 7,783,586 B2 | 8/2010 | Friedlander et al. |
| 2002/0004729 A1 | 1/2002 | Zak et al. |
| 2002/0106059 A1 | 8/2002 | Kroll et al. |
| 2003/0028536 A1 | 2/2003 | Singh et al. |
| 2003/0195394 A1 | 10/2003 | Saalsaa |
| 2003/0212575 A1 * | 11/2003 | Saalsaa et al. ............ 705/2 |
| 2006/0059423 A1 * | 3/2006 | Lehmann et al. .......... 715/530 |
| 2006/0122520 A1 | 6/2006 | Banet et al. |
| 2006/0167346 A1 | 7/2006 | Sarel |
| 2006/0173500 A1 | 8/2006 | Walker et al. |
| 2006/0178908 A1 | 8/2006 | Rappaport |
| 2007/0055559 A1 | 3/2007 | Clawson |
| 2007/0112275 A1 | 5/2007 | Cooke et al. |
| 2007/0116189 A1 | 5/2007 | Clawson |
| 2007/0201664 A1 | 8/2007 | Salafia et al. |
| 2009/0168975 A1 | 7/2009 | Clawson |
| 2009/0191529 A1 | 7/2009 | Mozingo et al. |
| 2010/0004710 A1 | 1/2010 | Kellum |
| 2010/0121156 A1 * | 5/2010 | Yoo ................ 600/300 |
| 2010/0152800 A1 | 6/2010 | Walker et al. |
| 2010/0198755 A1 * | 8/2010 | Soll et al. ............ 706/11 |
| 2010/0257250 A1 | 10/2010 | Salafia et al. |
| 2011/0064204 A1 * | 3/2011 | Clawson ................ 379/45 |
| 2011/0066002 A1 * | 3/2011 | Clawson ................ 600/300 |
| 2011/0099031 A1 * | 4/2011 | Nair ................ 705/3 |
| 2011/0215930 A1 * | 9/2011 | Lee et al. ............ 340/573.1 |
| 2012/0183128 A1 * | 7/2012 | Clawson ................ 379/45 |
| 2012/0207286 A1 * | 8/2012 | Clawson ................ 379/45 |
| 2012/0210271 A1 * | 8/2012 | Clawson ................ 715/780 |

FOREIGN PATENT DOCUMENTS

| | | |
|---|---|---|
| JP | 2003-187003 A | 7/2003 |
| JP | 2003256963 A | 9/2003 |
| JP | 2010033201 A | 12/2010 |
| KR | 20070043337 A | 4/2007 |
| WO | WO2006/015229 A2 | 2/2006 |
| WO | WO2008/156876 A1 | 12/2008 |

OTHER PUBLICATIONS

International Search Report and Written Opinion for PCT/US2011/042543 filed on Jun. 30, 2011, and mailed from ISA on Feb. 9, 2012, 11 pgs.

International Search Report and Written Opinion for PCT/US2011/042582 filed on Jun. 30, 2011, and mailed from ISA on Feb. 9, 2012, 8 pgs.

International Preliminary Report of Patentability for PCT/US2010/043308 filed on Jul. 27, 2010 mailed Mar. 22, 2012, 6 pgs.
International Preliminary Report of Patentability for PCT/US2010/043311 filed on Jul. 27, 2010 mailed Mar. 29, 2012, 6 pgs.
Office Action Summary from USPTO for U.S. Appl. No. 12/558,045 mailed Mar. 22, 2012, 9 pgs.
United States Patent Office, Office Action for U.S. Appl. No. 12/558,808 mailed Apr. 23, 2011.
Radosevich, Lynda, "Network holds sway on life, death," Computerworld, v27 n21, May 24, 1993, 2 pgs.
Harris, Roger, "Updated 911 Phone System Top Concern of Residents," Business First-Louisville, v9 n19 s1, Dec. 1992, 3 pgs.
"Geac Completes Software Install," Wireless Week, Nov. 18, 1996, 3 pgs.
"Dictaphone introduces Windows-based Computer-Aided Dispatch (CAD) system," Business Wire, Apr. 23, 1996, 2 pgs. (in commercial use in 1995).
Holroyd, Brian, et al., "Medical Control; Quality Assurance in Prehospital Care," JAMA, the Journal of American Medical Association, v256, n8, Aug. 1986, p. 1027-1031.
CBS web page News Story entitled "911 Operator: 'It's got to be Hell'", Mar. 31, 2006 (excerpts from 911 operators' actions during the attacks on Sep. 11, 2001), 3 pgs.
Best, Wendy, "999 United Emergency services share life-saving Role to boost response," Western Daily Press, WDP Severnside ed., May 27, 1999, 2 pgs.
Poellmitz, William C., "Wireless technology keeps public safety a step ahead," Nation's Cities Weekly, v21 n17, Apr. 27, 1998, 3 pgs.
Crowley, Mark, "Learning from CAD System Implementation," Communications, v29 n8, Aug. 1992, 5 pgs.
Anonymous, "Suburban Chicago towns centralize 911 services," Communications News, v31 n10, Oct. 1994, 2 pgs.
Office Action Summary from USPTO for U.S. Appl. No. 10/255,901 mailed Dec. 31, 2003, 8 pgs.
Office Action Summary from USPTO for U.S. Appl. No. 10/255,901 mailed Oct. 13, 2004, 8 pgs.
Office Action Summary from USPTO for U.S. Appl. No. 10/255,901 mailed Jun. 29, 2005, 7 pgs.
Advisory Action Before the Filing of an Appeal Brief from USPTO for U.S. Appl. No. 10/255,901 mailed Feb. 14, 2006, 3 pgs.
Office Action Summary from USPTO for U.S. Appl. No. 10/255,901 mailed Jun. 7, 2006, 8 pgs.
Office Action Summary from USPTO for U.S. Appl. No. 10/255,901 mailed Feb. 27, 2007, 8 pgs.
Office Action Summary from USPTO for U.S. Appl. No. 10/255,901 mailed Sep. 6, 2007, 9 pgs.
Office Action Summary from USPTO for U.S. Appl. No. 10/255,905 mailed May 19, 2004, 7 pgs.
Office Action Summary from USPTO for U.S. Appl. No. 10/255,905 mailed May 26, 2005, 5 pgs.
Office Action Summary from USPTO for U.S. Appl. No. 10/255,905 mailed Feb. 9, 2006, 8 pgs.
Advisory Action Before the Filing of an Appeal Brief from USPTO for U.S. Appl. No. 10/255,905 mailed Aug. 11, 2006, 3 pgs.
Office Action Summary from USPTO for U.S. Appl. No. 10/255,905 mailed Jan. 30, 2007, 7 pgs.
Notice of Non-Compliant Amendment (37 CFR 1.121) from USPTO for U.S. Appl. No. 10/255,905 mailed Jul. 9, 2007, 4 pgs.
Office Action Summary from USPTO for U.S. Appl. No. 10/255,905 mailed Oct. 5, 2007, 7 pgs.
Office Action Summary from USPTO for U.S. Appl. No. 09/685,697 mailed Jul. 18, 2003, 8 pgs.
Office Action Summary from USPTO for U.S. Appl. No. 09/685,697 mailed Feb. 3, 2004, 5 pgs.
Office Action Summary from USPTO for U.S. Appl. No. 09/685,697 mailed Jan. 4, 2005, 5 pgs.
Office Action Summary from USPTO for U.S. Appl. No. 09/685,697 mailed Oct. 4, 2005, 7 pgs.
Advisory Action Before the Filing of an Appeal Brief from USPTO for U.S. Appl. No. 09/685,697 mailed Mar. 13, 2006, 4 pgs.
Office Action Summary from USPTO for U.S. Appl. No. 09/685,697 mailed Jun. 26, 2006, 8 pgs.
Office Action Summary from USPTO for U.S. Appl. No. 09/685,697 mailed Apr. 10, 2007, 9 pgs.
Office Action Summary from USPTO for U.S. Appl. No. 09/685,697 mailed Oct. 9, 2007, 11 pgs.
Office Action Summary from USPTO for U.S. Appl. No. 10/140,635 mailed Oct. 3, 2003, 9 pgs.
Office Action Summary from USPTO for U.S. Appl. No. 10/140,635 mailed Jul. 16, 2004, 11 pgs.
Office Action Summary from USPTO for U.S. Appl. No. 10/140,635 mailed Apr. 19, 2005, 11 pgs.
Office Action Summary from USPTO for U.S. Appl. No. 10/140,635 mailed Jan. 17, 2006, 13 pgs.
Office Action Summary from USPTO for U.S. Appl. No. 10/140,635 mailed Sep. 20, 2006, 15 pgs.
Office Action Summary from USPTO for U.S. Appl. No. 10/140,635 mailed Jun. 21, 2007, 15 pgs.
International Search Report for PCT/US2008/054987 filed on Feb. 26, 2008, and mailed on Oct. 8, 2008, 2 pgs.
Written Opinion of the International Searching Authority for PCT/US2008/054987 filed on Feb. 26, 2008, and mailed on Oct. 8, 2008, 9 pgs.
Notification of Transmittal of the International Search Report (2 pgs.), International Search Report, (2 pgs.), and Written Opinion (8 pgs.) mailed from International Searching Authority on Jun. 10, 2009.
International Search Report and Written Opinion for PCT/US09/48577, International filing date Jun. 25, 2009, mailed from ISA Aug. 7, 2009, 9 pgs.
Office Action Summary from USPTO for U.S. Appl. No. 12/422,561 mailed Jul. 3, 2012, 23 pgs.
PCT Search Report and Written Opinion PCT/US2010/050402, Int'l Filing Date Sep. 27, 2010, mailed from International Searching Authority on Apr. 27, 2011, 9 pgs.
Office Action for U.S. Appl. No. 12/268,963, filed Nov. 11, 2008, mailed from USPTO on Jul. 29, 2011, 18 pgs.
International Search Report and Written Opinion mailed Jan. 19, 2011 in PCT Application No. PCT/US2010/043308, filed Jul. 27, 2010.
International Search Report and Written Opinion mailed Jan. 19, 2011 in PCT Application No. PCT/US2010/043311, filed Jul. 27, 2010.

* cited by examiner

BURN DIAGNOSTIC AND INTERVENTION TOOL FOR EMERGENCY DISPATCH

COPYRIGHT NOTICE

© 2010 Priority Dispatch Corp. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

TECHNICAL FIELD

This disclosure relates to computer systems and methods for providing medical protocol interrogation, instruction, and emergency dispatch. More specifically, the disclosure is directed to computer-implemented tools to assist a dispatcher during an interrogation and instruction of an emergency caller.

BRIEF DESCRIPTION OF THE DRAWINGS

Non-limiting and non-exhaustive embodiments of the disclosure are described, including various embodiments of the disclosure with reference to the figures, in which.

DETAILED DESCRIPTION

Figure 1:
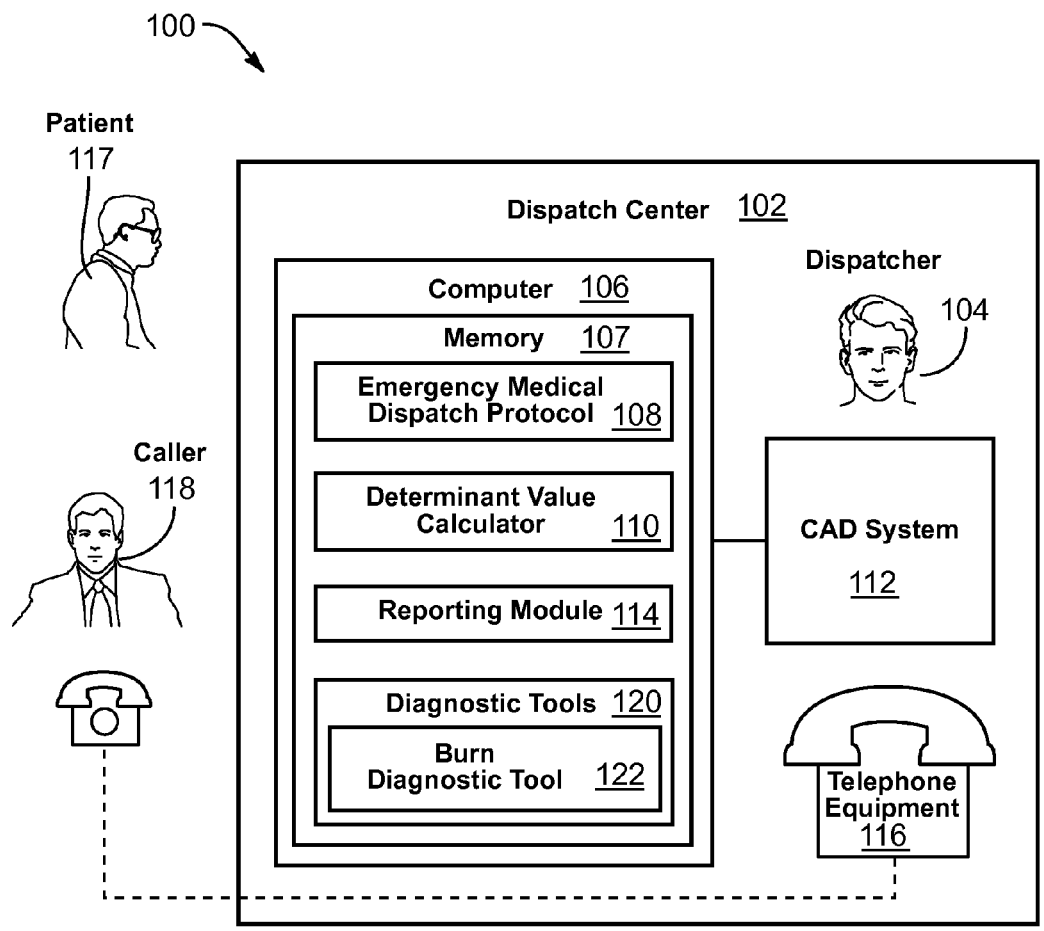
FIG. 1 is a block diagram of an emergency medical dispatch system, according to one embodiment.

Emergency dispatchers handle emergency calls reporting a wide variety of emergency situations. An automated emergency dispatch system, which may be implemented on a computer, can aid a dispatcher in prioritizing the calls and processing the calls to generate an appropriate emergency dispatch response. Regardless of the experience or skill level of the dispatcher, automated emergency dispatch systems can enable a consistent and predictable emergency dispatch response, despite the diverse aspects of emergency situations, including inter alia signs, symptoms, conditions, and circumstances, that may be reported from one call to the next.

Although an automated emergency dispatch system can enable collection and processing of widely divergent aspects of emergency situations, some of the emergency situations and/or aspects reported should be explored in greater depth as they are reported. This further exploration may require the dispatcher to probe more deeply to gather more descriptive details. Moreover, some emergency situations may be improved by more detailed instructions. Still other emergency situations may involve a clinical presentation of a condition that is not easily diagnosed, but which could alter the appropriate dispatch response if properly diagnosed.

A dispatcher with little or no medical training or experience likely cannot properly explore situations and/or aspects or diagnose medical conditions, let alone instruct a caller to do so. Furthermore, the automated emergency dispatch systems are not equipped to assist or enable a dispatcher to explore situations in greater depth, to provide further instruction, or to diagnose conditions. Accordingly, the present disclosure is directed to diagnostic tools that supplement an automated emergency dispatch system to attempt to address these and other shortcomings of automated emergency dispatch systems.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer executable code located within a memory device and/or computer-readable storage medium. A software module may, for instance, comprise one or more physical or logical blocks of computer instructions, which may be organized as a routine, program, object, component, data structure, etc. that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools.

An emergency dispatch system as disclosed herein may be computer-implemented in whole or in part on a digital computer. The digital computer includes a processor performing the required computations. The computer further includes a memory in electronic communication with the processor for storing a computer operating system. The computer operating systems may include MS-DOS, Windows, Linux, Unix, AIX, CLIX, QNX, OS/2, and Apple. Alternatively, it is expected that future embodiments will be adapted to execute on other future operating systems. The memory also stores application programs including a Computer Aided Dispatch (CAD) program, an automated emergency dispatch protocol, a user interface program, and data storage. The computer may further include an output device, such as a display unit, for viewing the displayed instructions and inquiries, and a user input device for inputting response data.

FIG. 1 is an emergency medical dispatch system 100, according to one embodiment. At a dispatch center 102, a dispatcher 104 may operate a computer 106. The computer 106 may include a memory 107 to store protocols, modules, tools, data, etc. The computer 106 may be configured to execute an emergency medical dispatch protocol 108 to enable the dispatcher 104 to rapidly and consistently address a medical emergency of a patient 117 as reported by a caller 118. The emergency medical dispatch protocol 108 provides a logic tree with questions, possible responses from a caller 118, and instructions to the caller 118. The responses may route to subsequent questions and/or instructions to the caller. The responses are processed according to predetermined logic to provide to the dispatcher 104 the correct emergency medical dispatch response (e.g., by trained emergency responders) and the appropriate doctor-approved post-dispatch instructions for relay to the caller 118 before professional help arrives at the scene. The emergency medical dispatch system 100 may also aid the dispatcher in determining an appropriate priority of the emergency call, including but not limited to a priority of the emergency call relative to other emergency calls.

Although an emergency medical dispatch system 100 and emergency medical dispatch protocol 108 are disclosed and described herein, a person of ordinary skill can appreciate that other emergency dispatch systems and emergency dispatch protocols are contemplated, including but not limited to emergency fire dispatch systems and protocols and emergency police dispatch systems and protocols. Exemplary embodiments of such emergency dispatch systems and protocols are disclosed in U.S. Pat. Nos. 5,857,966, 5,989,187, 6,004,266, 6,010,451, 6,053,864, 6,076,065, 6,078,894, 6,106,459, 6,607,481, 7,106,835, and 7,428,301, which are incorporated herein by reference.

The computer 106 may also operate a determinant value calculator 110 to calculate a determinant value from the responses of the caller 118 to protocol questions. The computer 106 presents the determinant value to generate an appropriate emergency dispatch response and/or establish the priority of the emergency call. The response may include dispatching professional emergency responders to the scene of the emergency. Because the questions asked and the recommendations that are made deal directly with life and death decisions, the protocols used shall have passed through a rigorous medical review by a panel of doctors and EMS public safety experts who specialize in emergency medicine. The determinant value calculator 110 may be stored on the memory 107 of the computer.

Many calls for medical services are not true medical emergencies, so it is important to prioritize the calls in several ways. First, calls that are true emergencies should be dispatched first. Second, if an agency has units with different capabilities, the more advanced units should be sent to more severe medical problems. And finally, if lights-and-siren are not needed from a medical standpoint, they should not be used, thereby increasing the safety of all those on the road and in the emergency vehicles. While many medical calls are not true emergencies, all situations can benefit from medical evaluation and instruction. Prior to the arrival of professional help on-scene, the emergency medical dispatch protocol 108 can provide the dispatcher 104 with instructions for the caller 118 that are appropriate to the type of call, from a patient 117 with minor lacerations to a patient 117 who is not breathing.

The determinant value provides a categorization code of the type and level of the incident. The code may be provided to a Computer Aided Dispatch (CAD) system 112 for processing. The CAD system 112 is a tool used by a dispatcher 104 to track and allocate emergency response resources. The CAD system 112 may operate in whole or in part on a separate computer in communication with the computer 106. In another embodiment, the CAD system 112 operates on the computer 106. The primary information used by the CAD system 112 is location information of both the incident and units, unit availability and the type of incident. The CAD system 112 may use third party solutions, vehicle location transponders and mobile data terminals (MDT's) for automating the location and availability tasks. The CAD system may also use an emergency dispatch protocol 108 to facilitate structured call taking for incident interrogation, as previously described.

The computer 106 may also include a reporting module 114 to statistically measure the performance of individual staff and overall performance of the dispatch center 102. These statistics include compliance rates, call processing statistics, and peer measurements. The reporting module 114 may be stored on the memory 107 of the computer 106.

The computer 106 may further comprise an input device such as a keyboard, mouse, or other input device and also an output device such as a display monitor. The input device receives input from a user (generally a dispatcher) and provides it to the emergency medical dispatch system 100. The input may be provided to the computer 106, the emergency protocol 108, the diagnostic tools 120, and/or the CAD system 112. An output device receives output from the emergency medical dispatch system 100 and displays or otherwise presents the output to the user. In another embodiment, the input device and the output device are provided by the CAD system 112. In still another embodiment, the CAD system 112 runs on the computer 106.

The dispatch center 102 includes telephony equipment 116 to answer emergency calls. A call into the dispatch center 102 from a caller 118 may initiate creation of a medical call incident. The dispatcher 104 identifies the call as requiring an emergency medical dispatch, and the emergency medical dispatch protocol 108 is accessed. The protocol 108 may provide instructions that are expertly drafted to assist a novice caller 118 in diagnosing a condition of a patient 117. The protocol 108 may also provide expertly drafted first aid instructions to assist a patient 117 prior to the arrival of trained emergency responders. The instructions may be vocally relayed by the dispatcher 104 to the caller 118 over the telephony equipment 116.

Some of the questions presented by the emergency medical dispatch protocol 108 may be readily answerable by the caller 118, whereas others are more difficult to answer. Certain diagnostic inquiries may be difficult for the untrained caller to determine or may be difficult to answer under the stress of an emergency situation. For example, the caller may have a difficult time estimating the percentage of a patient's body that has been burned. Accordingly, in addition to instructions, the emergency medical dispatch system 100 may provide one or more computer-implemented diagnostic tools 120. The diagnostic tools 120 may greatly improve information collection and intervention for emergency medical response situations and aid in saving lives.

A diagnostic tool 120 may aid the dispatcher 104 and/or the caller 118 (via instructions from the dispatcher 104) in diagnosing a condition of a patient 117. A diagnostic tool 120 may also be an interventional tool, providing instructions that direct a caller 118 to intervene, or take action, to treat a patient 117, or otherwise change the circumstances or conditions of an emergency situation. For sake of clarity, diagnostic tools and interventional tools are both referred to herein generally as diagnostic tools. Accordingly, a diagnostic tool 120, as referred to herein, may provide diagnostic instructions, interventional instructions, or both diagnostic and interventional instructions. Whether a diagnostic tool 120 provides merely diagnostic instructions, merely interventional instructions, or both diagnostic and interventional instructions, the diagnostic tool can provide consistent and reliable instruction, information gathering, and/or timing for a particular emergency situation.

The diagnostic tools 120 are computer implemented software modules that enable a dispatcher 104 to provide consistent, expert advice to assist a caller with regards to a particular aspect of an emergency situation. In highly stressful conditions, the diagnostic tools 120 provide a necessary resource to reading critical signs. The diagnostic tools 120 may be stored in the memory 107 of the computer 106 and initiated and executed as required. The diagnostic tools 120 may be embodied as computer executable software applications and associated data.

The emergency medical dispatch protocol 108 may call on a diagnostic tool 120, for example, to assist with an interrogatory, and may route to the appropriate diagnostic tool 120 when needed. When directed according to the protocol 108, the emergency medical dispatch system 100 may automatically, i.e., without dispatcher intervention, initiate the appropriate diagnostic tool 120 on the dispatch center computer 106. This may occur when the emergency medical dispatch protocol 108 arrives at a diagnosis step in the protocol and initiates a corresponding diagnostic tool 120. The emergency dispatch system 100 may also allow the dispatcher 104 the option to manually call upon a diagnostic tool 120 as desired. Icons and/or buttons may be displayed in a tool bar, or other convenient location on a user interface to allow the dispatcher 104 to initiate a corresponding diagnostic tool 120. In another embodiment, the emergency medical dispatch protocol 108 may simply prompt the dispatcher 104 to launch the appropriate diagnostic tool 120 when needed.

The diagnostic tool 120 discussed herein comprises a burn diagnostic tool 122. The burn diagnostic tool 122 may be configured to facilitate assessing the severity of a burn. The severity of a burn may be determined based on such factors as the burn surface area, the location of the burn, and/or the degree (or depth) of the burn. Individuals vary in size and shape. To account for these inequities in size and shape, a burned surface area may be calculated as a percentage of total body area. The burn diagnostic tool 122 may assist the dispatcher 104 in calculating the size of a burn, identifying the location, and/or guiding the caller in gauging (or estimating) the degree (or depth) of the burn. The burn diagnostic tool 122 is discussed below with reference to figures of graphical user interfaces that exemplify certain embodiments. One of skill in the art will appreciate that such interfaces may be implemented and designed in various ways.

Figure 2:
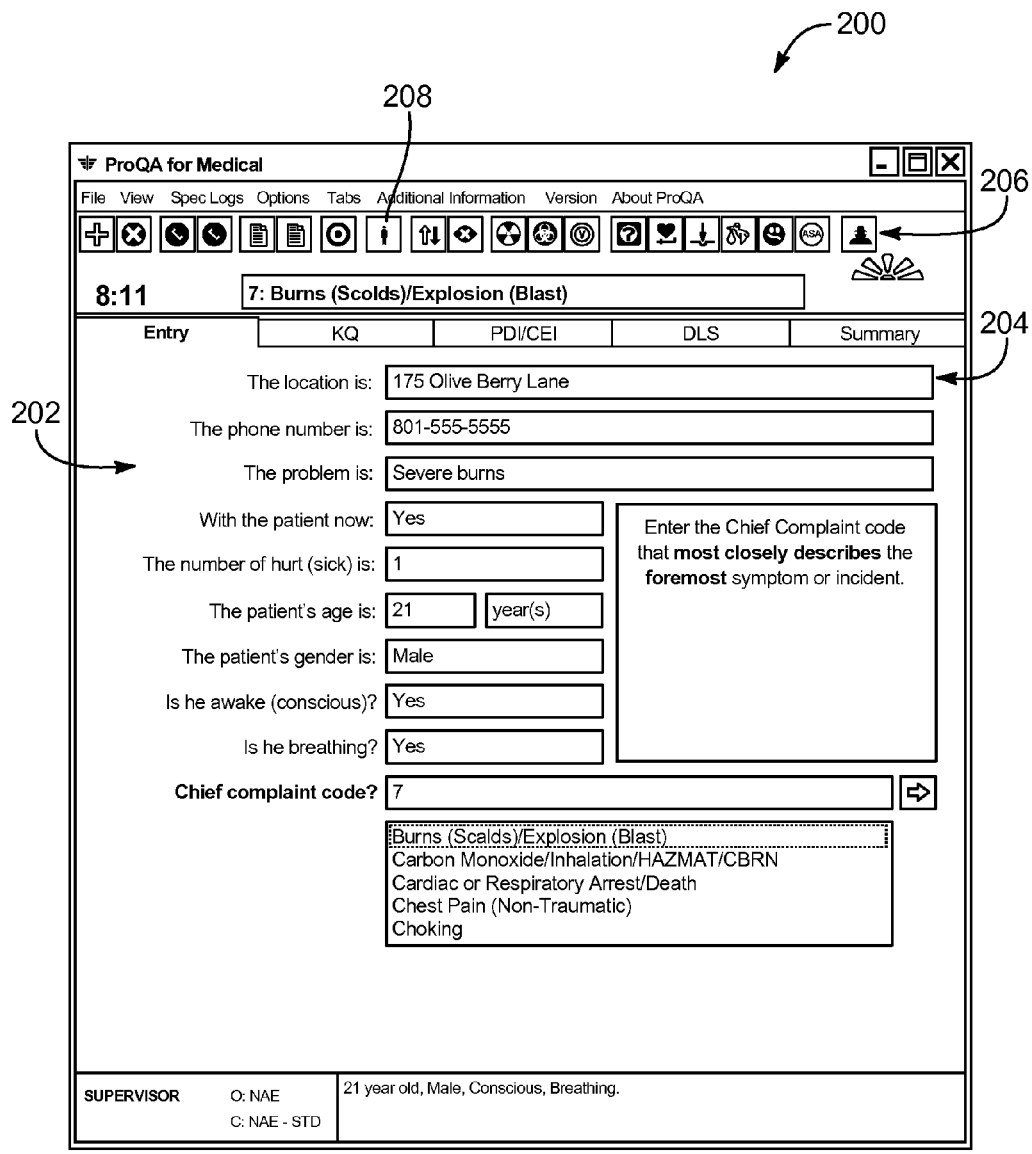
FIG. 2 is a user interface of an emergency medical dispatch system, according to one embodiment.

FIG. 2 illustrates a user interface 200 of an emergency medical dispatch protocol, according to one embodiment. The emergency medical dispatch protocol user interface 200 allows a dispatcher to interface with the emergency medical dispatch protocol. The emergency medical dispatch protocol may present interrogatories 202 via the emergency medical dispatch protocol user interface 200. The interrogatories 202 are provided for the dispatcher to direct to the caller to gather information regarding the medical emergency of the patient. The dispatcher and/or the emergency medical dispatch system may gather the information in the form of caller responses to the interrogatories 202. The dispatcher may input the caller's responses to the interrogatories into response fields 204 provided by the user interface 200. The response fields 204 may include, for example, familiar user interface components, including but not limited to text fields, text boxes, menus, drop-down menus, drop-down selection boxes, lists, buttons, check boxes, and radio buttons. The response fields 204 may correspond to information indicative of one or more responses of the caller to the interrogatories 202.

The caller responses, and information therein, relayed from the caller to the dispatcher, and input into the system, may be used by the emergency medical dispatch protocol to determine subsequent interrogatories 202 and instructions to present to the dispatcher. The caller responses, and information therein, may indicate the caller's observations of signs and symptoms of the patient's medical condition. The information gathered from the caller responses may be used by the emergency medical dispatch system to generate an emergency medical dispatch response by trained emergency responders. The information gathered from the caller responses may be used by the determinant value calculator to calculate a determinant value that can be communicated to the emergency responders. Further details of emergency medical dispatch protocols and user interfaces to interact with the same can be found in the earlier referenced U.S. patents.

The emergency medical dispatch system user interface 200 may also provide one or more diagnostic tool launch inputs 206. As illustrated, one or more buttons may be provided on the user interface as diagnostic tool launch inputs 206. As will be appreciated by a person of ordinary skill, the diagnostic tool launch inputs 206 may comprise a component other than a button, including familiar user interface components such as a drop down menu, a drop down selection box, a list, a check box, and a radio button. The diagnostic tool launch inputs 206 enable the dispatcher to launch a particular diagnostic tool. Although the emergency medical dispatch protocol may automatically initiate a diagnostic tool based on dispatcher-entered input indicative of one or more responses of the caller, the diagnostic tool launch inputs 206 provide a way for the dispatcher to manually (i.e. anytime, at the dispatcher's discretion) initiate a diagnostic tool. In FIG. 2, the user interface provides a burn diagnostic tool launch input 208. The burn diagnostic tool launch input 208 comprises a button on the emergency medical dispatch system user interface 200. The button may include an icon, such as an image of a match, to indicate that the button is the burn diagnostic tool launch input 208 that manually initiates the burn diagnostic tool.

Figure 3:
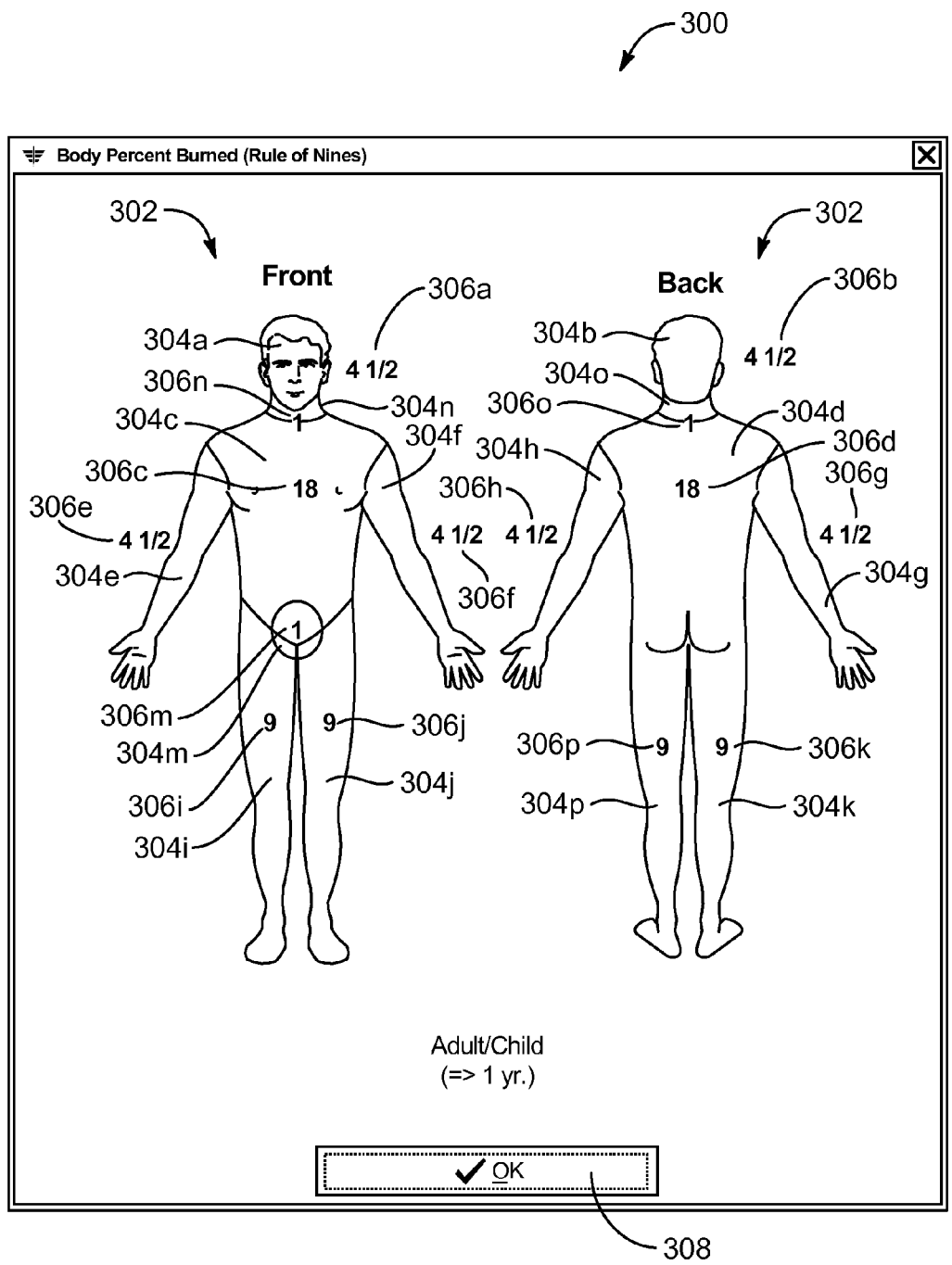
FIG. 3 is one embodiment of a user interface of a burn diagnostic tool.

FIG. 3 illustrates an embodiment of a user interface 300 of a burn diagnostic tool, according to one embodiment. The user interface 300 may be configured to assist a dispatcher in determining the burn surface area of a burn on a patient. When an emergency caller reports that a patient has been burned, the appropriate level of emergency response may depend largely on the severity of the burn. A difficulty arises in that often emergency callers are not skilled in determining or describing the severity of a burn. Accordingly, a question from the dispatcher such as, "How severe are the patient's burns?" may not successfully elicit the information the dispatcher may need to dispatch an appropriate emergency response. Similarly, the dispatcher may lack skill and experience to properly inquire and guide the caller in estimating the severity of the patient's burns.

As previously described, the severity of a burn is determined based on the burn surface area and the degree (or depth) of the burn. With an estimate of a burn surface area, a medical professional can quickly determine how serious the patient's burns are and how urgently the patient may need medical care. Similarly, emergency dispatch protocols may be enabled to prompt and/or dispatch an appropriate emergency response based on a burn surface area estimate.

Although a burn surface area estimate is readily proportional to the severity of the burn and the level of medical care the patient is in need of, estimating burn surface area may not be trivial for an untrained emergency caller and/or a dispatcher handling a burn-related emergency call. Accordingly, the burn diagnostic tool can prompt the dispatcher to apply a method or guide the caller in applying a method, to calculate or otherwise estimate the burn surface area of the patient's burns. One such method is referred to herein as the "Rule of Nines." The Rule of Nines methodology is discussed more fully below, but a person of ordinary skill in the art will recognize that the present disclosure is not limited to the Rule of Nines methodology. When an emergency caller reports that a patient has been burned, the burn diagnostic tool may be manually launched by the dispatcher or automatically launched by the emergency dispatch protocol. The manner by which the burn diagnostic tool can aid in determining the severity of the patient's burns will be made apparent by the following description of the illustrated embodiment.

The user interface 300 of a burn diagnostic tool illustrated in FIG. 3 provides a portrayal of a human body 302 that is divided into a plurality of sections 304a-p. The portrayal of the human body 302 enables the dispatcher to quickly visualize the body of the patient. While the caller may be able to view the actual patient, the portrayal of a human body 302 allows the dispatcher to better visualize what the caller is seeing. Labels 306a-p may also be provided for the plurality of sections 304a-p. In the illustrated embodiment, an adult human body is portrayed. In another embodiment, the human body portrayed may be that of a child or an infant. Because the proportions of an adult human body are different than the proportions of the body of a child or of an infant, the visual portrayal enables the dispatcher to more quickly visualize and ascertain the seriousness of a burn on a particular section of the patient's body.

The portrayal of the human body 302 can be divided into a plurality of sections 304a-p to facilitate calculating or otherwise determining the burn surface area of a patient. A caller can relay to the dispatcher over the phone that a particular section of the patient's body is burned, and the dispatcher can visualize the section that is burned by viewing the corresponding section of the plurality of sections 304a-p. For example, the caller may indicate to the dispatcher that the patient's entire right arm is burned. By viewing the right arm on the portrayal of the human body 302, the dispatcher can quickly estimate the seriousness of the patient's burn. Specifically, the dispatcher can visualize the surface area of the arm by comparison to the rest of the body and recognize that, while serious, a burn on the entire right arm may not be life threatening.

In another embodiment, the burn diagnostic tool may prompt the dispatcher to instruct the caller to identify to the dispatcher only the burned sections that have burns of a particular degree (depth). The instruction provided by the user interface may further guide the caller as to how to identify or distinguish between first degree, second degree, and third degree burns. For example, the user interface 300 may provide an instruction directing the caller to "Please identify the areas of the patient's body that are burned and the burned flesh is blistered or charred." The instruction may aid filtering out patients suffering from mild sunburns, which may cover a large surface area yet lack the degree or classification to need urgent medical attention.

The burn diagnostic tool can further assist a dispatcher in determining the severity of a burn by facilitating application of a method to approximate and quantify the severity. In the illustrated embodiment, the portrayal of the human body 302 on the user interface 300 is divided into a plurality of sections 304a-p according to the Rule of Nines. The Rule of Nines is a method or scale that can be used to approximate a burn surface area by dividing the body into sections of 9 percent, or multiples of 9 percent, of the total surface area of the human body—i.e. sections of "nines." For example, in the illustrated embodiment, the portrayal of the human body 302 may be divided into the following sections and corresponding approximate percentages of the total surface area:

| Section | Percentage (%) |
| --- | --- |
| face (front of head) 304a | 4.5 |
| back of head 304b | 4.5 |
| chest/abdomen 304c | 18 |
| back 304d | 18 |
| front of right arm 304e | 4.5 |
| front of left arm 304f | 4.5 |
| back of right arm 304g | 4.5 |
| back of left arm 304h | 4.5 |
| front of right leg 304i | 9 |
| front of left leg 304j | 9 |
| back of right leg 304k | 9 |
| back of left leg 304p | 9 |
| genitalia 304m | 1 |
| front of neck 304n | 1 |
| back of neck 304o | 1 |

Each of the sections represents a multiple of 9 percent of the total surface area of the body, pursuant to the Rule of Nines, except the genitalia and neck sections, which each account for approximately 1 percent of the total surface area.

The sections 304a-p of the portrayal of the human body 302 aid the dispatcher in applying the Rule of Nines by enabling the dispatcher to visualize sections of the body. The sections break out the calculation into manageable sections for which the surface area can easily be estimated. Moreover, the surface area for each section is easily remembered because it is a multiple of nine. When the emergency caller reports to the dispatcher that the patient's entire right arm is burned, the dispatcher can readily estimate that the burn surface area is 9 percent. The estimate of the burn surface area quantifies the severity of the burn.

In another embodiment, the human body may be divided into eleven sections, such that each of the eleven sections is approximately equal to 9 percent of the total surface area of the human body. The eleven sections may include: head, right arm, left arm, chest, abdomen, upper back, lower back, front of right leg, front of left leg, back of right leg, and back of left leg. The eleven sections account for 99 percent of the total surface are of the human body. A twelfth section may be included to encompass the genitalia and thus account for the last 1 percent of the total surface area of the body. Still additional sections may be included to encompass other small areas of the body such as the neck area. These sections may account for a small percentage of the total surface area of the body, such as 1 percent.

In another embodiment, the body may be divided into eleven sections in a different manner. For example, the eleven sections may include: head, right arm, left arm, chest, abdomen, upper back, lower back, right thigh, left thigh, right leg (below the knee), and left leg (below the knee). Again, additional sections may be contemplated to encompass particular sections of the body, such as genitalia, while remaining substantially consistent with the Rule of Nines.

As will be appreciated, a number of methods of dividing the body into sections consistent with the Rule of Nines may be possible. One objective in making a division may be to provide an intuitive and natural division that can be easily remembered and that can enable easy approximation of the surface area of the section to allow quick calculation of a burn surface area of a burn victim.

The user interface 300 of the burn diagnostic tool may further provide an indication of the percentage of the total surface area that each of the plurality of sections 304$a$-$p$ represents. In the illustrated embodiment, the user interface 300 provides labels 306$a$-$p$ to indicate the percentage represented by each section. For example, the face label 306$a$ indicates that the surface area of the face is approximately 4.5 percent of the total surface area of the body. Similarly, the chest/abdomen label 306$c$ indicates that the surface area of the chest and abdomen is approximately 18 percent. Using the labels 306$a$-$p$, a dispatcher can quickly sum the percentages for all the sections that the caller reports are burned on the patient. For example, suppose a caller reports to the dispatcher that a patient has suffered burns on the entire right arm, entire right leg, and right half of the abdomen and chest areas. Using the burn diagnostic tool, the dispatcher can quickly calculate that the burn surface area of the burn on the patient. The dispatcher simply launches the tool and notes the percentages indicated by the labels for each of the corresponding sections as provided by the user interface 300. In particular, the dispatcher can note labels 306$e$ (4.5%) for the front of right arm section 304$e$, 306$g$ (4.5%) for the back of right arm section 304$g$, 306$i$ (9%) for the front of right leg section 304$i$, 306$k$ (9%) for the back of right leg section 304$k$, and 306$c$ (18%) for the chest/abdomen section 304$c$. The dispatcher can easily sum the noted percentages to determine that the burn surface area is approximately 36 percent (4.5% for front right arm+4.5% for back right arm+9% for front right leg+9% for back right leg+9% for half of chest/abdomen=36%).

The user interface 300 further provides an "OK" input 308. The OK input 308 enables the dispatcher to indicate to the diagnostic tool that the dispatcher is finished with the tool. Clicking the OK input 308 may close the tool.

Figure 4:
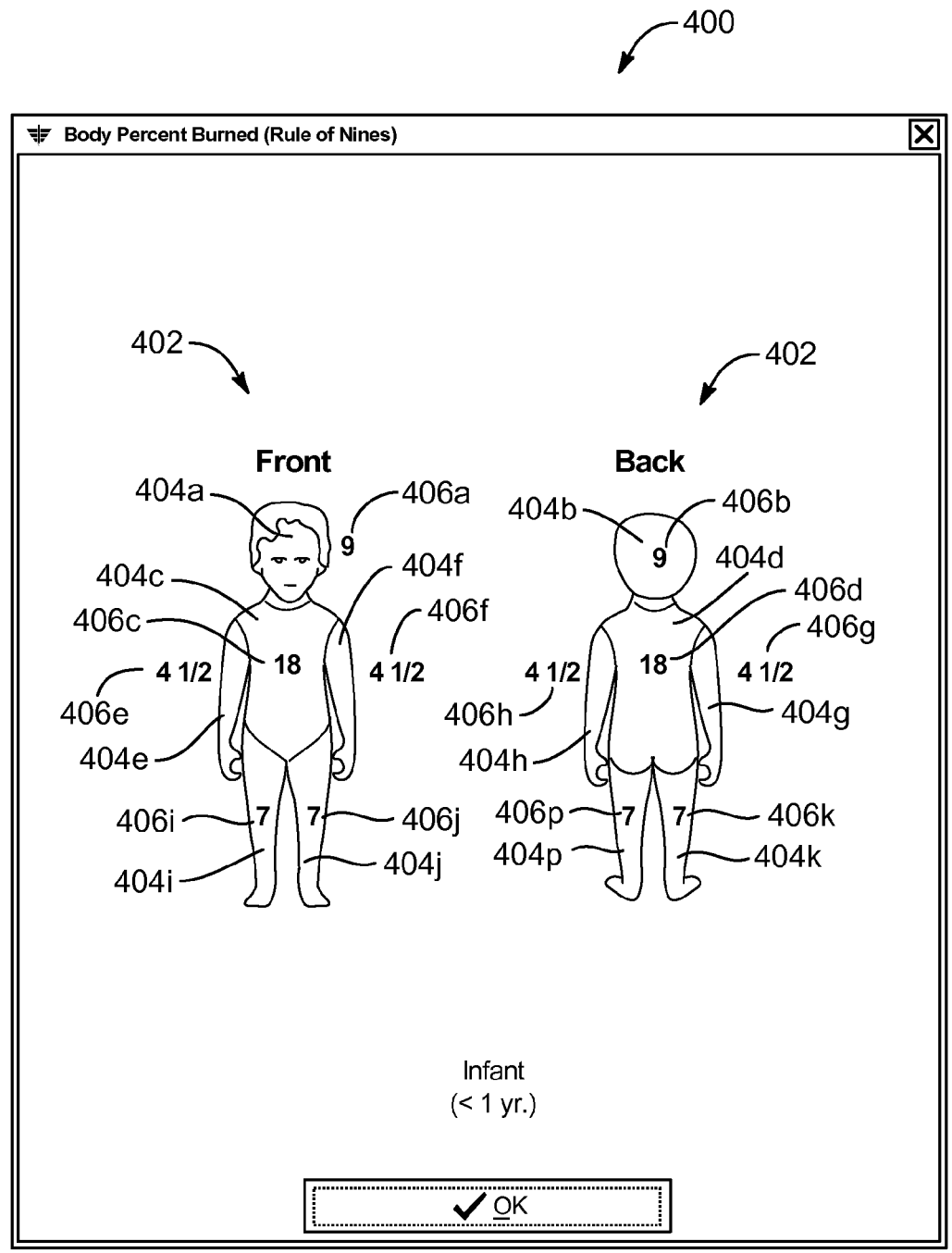
FIG. 4 is another embodiment of a user interface of a burn diagnostic tool.

Other portrayals of the human body may be appropriate to present depending on the age of the patient. For example, FIG. 4 is a user interface 400 presenting a portrayal of a human body 402 that is in the form of an infant. The portrayal of the infant human body 402 may be divided into a plurality of sections 404$a$-$p$, similar to the plurality of sections 304$a$-$p$ of FIG. 3. The plurality of sections 404$a$-$p$ of the embodiment of FIG. 4 may also be labeled with labels 406$a$-$p$.

The portrayal of an infant human body 402 may be appropriate because the proportions of the body of a child or an infant are different than the proportions of an adult human body. In particular, an infant's head is a larger proportion of an infant's body than the head of an adult is relative to an adult body. Also, the legs of a child or infant may be relatively shorter in proportion to the rest of the body than the legs of an adult. Because the proportions are different, a strict application of the Rule of Nines may not be appropriate for an infant patient. Accordingly, in the illustrated embodiment, the face (front of head) section 404$a$ and the back of the head section 404$b$ each represent approximately 9 percent of the total body surface area (as compared to 4.5 percent for an adult). Similarly, the front of the leg sections 404$i$, 404$j$ and the back of the leg sections 404$k$, 404$p$ each represent approximately 7 percent of the total body surface area (as compared to 9 percent for an adult).

The diagnostic tool may be automatically launched based on input received by the emergency dispatch protocol or may be manually launched by a dispatcher providing a launch input. Whether the diagnostic tool, upon launching, presents a user interface 300 with a portrayal of an adult human body 302 (as shown in FIG. 3) or a user interface 400 with a portrayal of an infant human body (as shown in FIG. 4) may depend on input received regarding the age of the patient. Referring briefly back to FIG. 1, the user interface 200 of the emergency dispatch protocol may be configured to receive information regarding the patient's age. The age information may be provided by the dispatcher. The age information may also be provided by a CAD system routing previously obtained information to the emergency dispatch protocol. The emergency dispatch protocol, or the dispatch center computer system running the protocol, may communicate to the burn diagnostic tool information relating to the age of the patient. The age information received or otherwise available to the diagnostic tool may influence the type of user interface presented by the diagnostic tool.

If age information available to the emergency dispatch protocol and/or the diagnostic tool indicates the patient is an adult, the diagnostic tool may present a user interface 300 with a portrayal of an adult human body 302. If the age information indicates the patient is an infant, the diagnostic tool may present a user interface 400 with a portrayal of an infant human body 402. If no age information is available, the diagnostic tool may present a default user interface. For example, the user interface 300 with a portrayal of an adult human body may be presented as a default user interface in the case that no age information is available.

Figure 5:
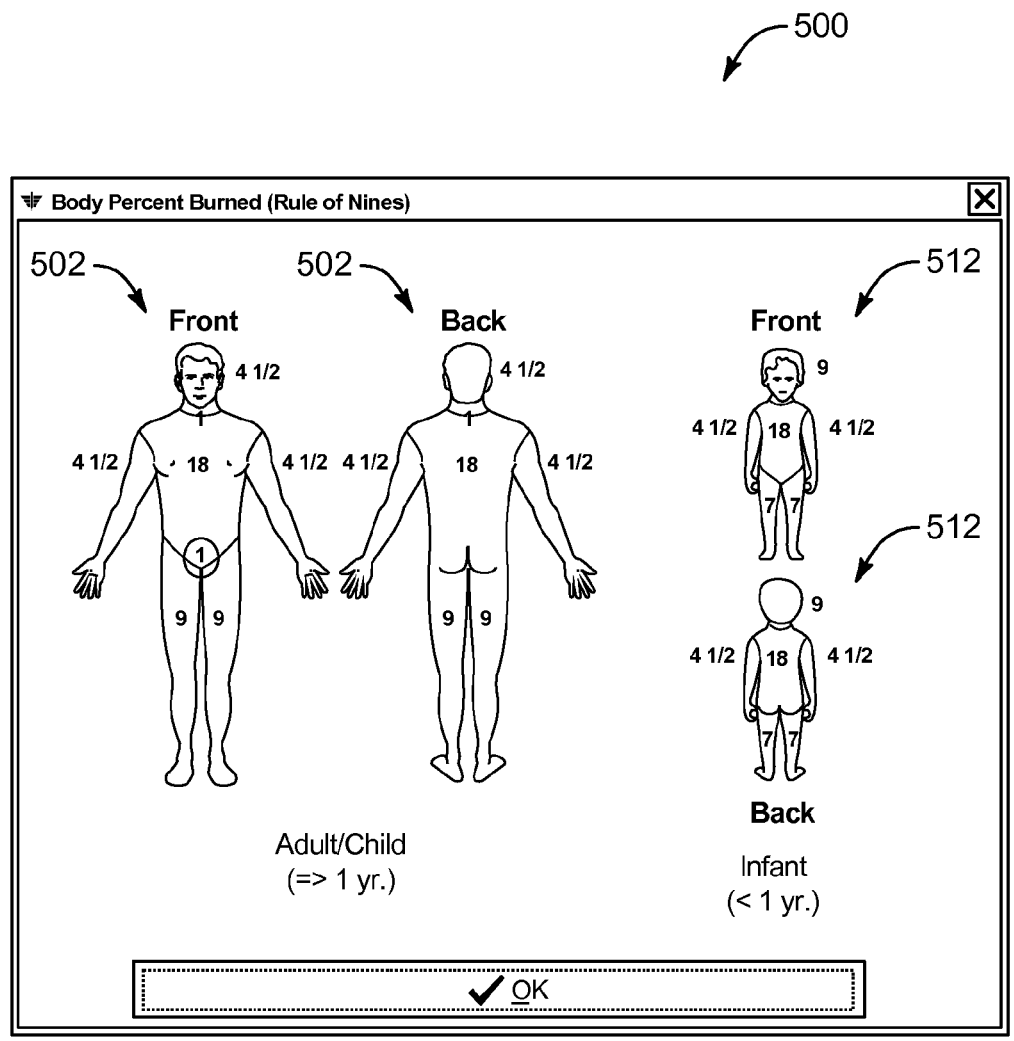
FIG. 5 is another embodiment of a user interface of a burn diagnostic tool.

FIG. 5 illustrates another embodiment of a user interface 500 presenting a portrayal of an adult human body 502 and also a portrayal of an infant human body 512. The user interface 500 may be presented by the diagnostic tool when patient age information may be missing, unavailable, or ambiguous. For example, the patient may be a small child and may be unconscious. Accordingly, the caller may be unable to relay to the dispatcher the age of the patient. Thus, the diagnostic tool may simply present the user interface 500 with portrayals 502, 512 of both an infant and adult human body so that both kinds of portrayal are available to the dispatcher. Similarly, the patient's age may be near the age at which the diagnostic tool distinguishes between infant/child and adult; i.e. one year old in the illustrated embodiment. When the patient's age is near the dividing age, the diagnostic tool may present the user interface 500 with portrayals of both an infant and an adult human body so that both types of portrayal are available to the dispatcher. With portrayals 502, 512 of both an infant and an adult available, the dispatcher may be prompted to inquire of the caller as to the approximate age of the patient and/or ask the caller to describe the patient's body or otherwise obtain information to utilize the appropriate portrayal 502, 512.

Although the user interfaces described above comprise portrayals of adult and infant human bodies, other portrayals are possible. For example, a user interface may provide a portrayal of the body of the patient based on other factors such as gender or based on specific statistics about the patient, including but not limited to height and weight. For example, if the patient is female, the diagnostic tool may present the body of a female. As another example, the diagnostic tool may present a body having proportions that approximate the height and weight of the patient.

Figure 6A:
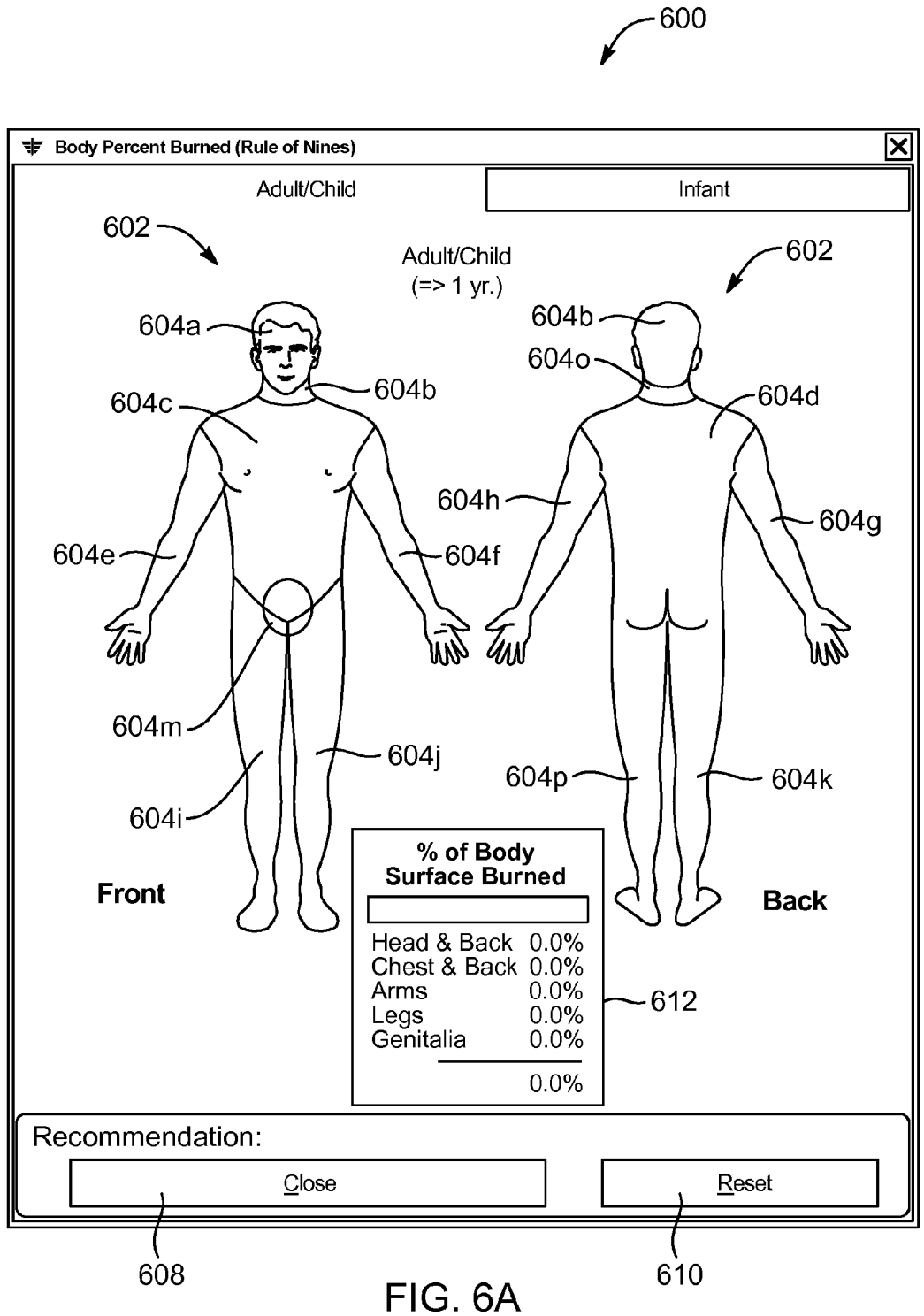
FIGS. 6A and 6B are another embodiment of a user interface of a burn diagnostic tool.
Figure 6B:
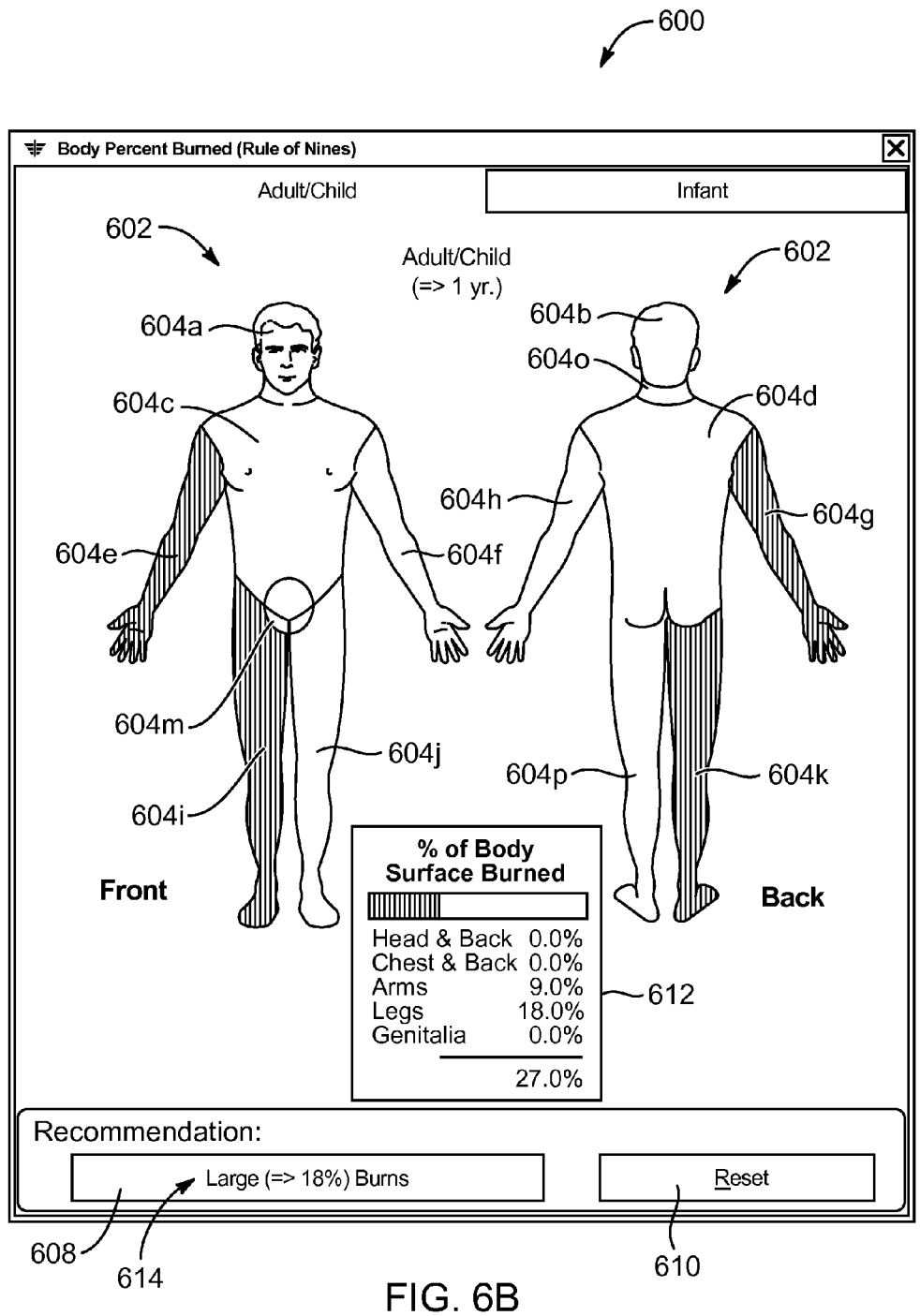

FIGS. 6A and 6B are another embodiment of a user interface, in which the plurality of sections 604a-p comprise input fields. A user of the diagnostic tool can simply select (e.g., click on) a section 604a-p on the portrayal of the human body 602 to indicate to the tool that the patient is burned on that particular section of the body. The input fields may comprise clickable areas on each of the plurality of sections 604a-p that a user can click on with the mouse to select the section. For example, if the caller relays to the dispatcher that the patient's entire left arm is burned, the dispatcher can select the front of left arm section 604f and the back of left arm section 604h. Selecting the sections indicates to the diagnostic tool that these sections of the patient are burned. A section 604a-p that has been selected may be shown as shaded or colored, as shown in FIG. 6B, to indicate to the dispatcher that the section was selected. The dispatcher may click a selected section a second time to unselect the section.

The diagnostic tool can sum the percentages of the selected sections to determine the burn surface area of the patient's burns. A calculation display 612 may be provided to indicate the sum of the percentages of the selected sections. The calculation display 612 may update each time a section 604a-p is selected. Alternatively, clicking an input 608 may indicate to the diagnostic tool that the dispatcher has provided all pertinent input and the diagnostic tool can perform the summing operation of the percentages of all selected sections and/or output the burn surface area calculation. The diagnostic tool may provide the result of the calculation to the emergency dispatch protocol.

In FIG. 6A, none of sections 604a-p have been selected. Accordingly, the calculation display 612 indicates that the percentage of the body surface area that is burned is 0%. The user interface 600 may provide a reset input 610, such as a button, which when clicked will return the interface to the state shown in FIG. 6A, with none of the sections 604a-p selected and the calculation display indicating 0%. Also, when none of the sections are selected, an input 608 may be provided to close the burn diagnostic tool. The input 608 may comprise a button, as illustrated in FIGS. 6A and 6B. Upon selection of a section 604a-p, the function of the input 608 may convert or change to also indicate to the tool that all pertinent input has been provided.

In FIG. 6B, the front right arm section 604e, the back right arm section 604g, the front right leg section 604i, and the back right leg section 604k have been selected. These sections are shaded to indicate they are selected. The calculation display 612 is updated to indicate that the percentage of the body surface area that is burned is 27%. The input 608 may also be provided to close the tool and communicate the burn surface area percentage to another system or protocol, such as the emergency medical dispatch system. The user interface 600 may also provide a display 614 to indicate to the dispatcher the severity of the burn, based on the burn surface area. In FIG. 6B, the display 614 is included as part of input 608. A person of ordinary skill in the art will recognize that the display 614 may be positioned elsewhere on the user interface 600. The display 614 indicates that the severity of the burn is "Large (=>18%) Burns." A person of ordinary skill in the art will recognize that the display may comprise other than the words illustrated. For example, the display 614 may include a variety of elements to convey the severity of the burn, such as a bar, a graph, a pie chart, color, shapes, and symbols.

As can be appreciated, other methods and means of providing input to the diagnostic tool are possible. For example, check boxes may be provided as input fields. A check box may be positioned to correspond to each of the plurality of sections of the portrayal of the human body. As another example, the check boxes may be provided in a list of body sections with an accompanying label to indicate the section corresponding to the check box. The dispatcher may simply check the check box for each section of the patient that is burned. The diagnostic tool can then receive the input and determine from the input the burn surface area of the patient's burns. The dispatcher can click on an input, such as a button, to indicate to the diagnostic tool that all input has been provided and the diagnostic tool can perform the calculation. Other inputs, such as a "Sum" input or a "Total" input, may be provided by the user interface to indicate to the diagnostic tool to perform the calculation or otherwise determine the burn surface area.

Figure 7:
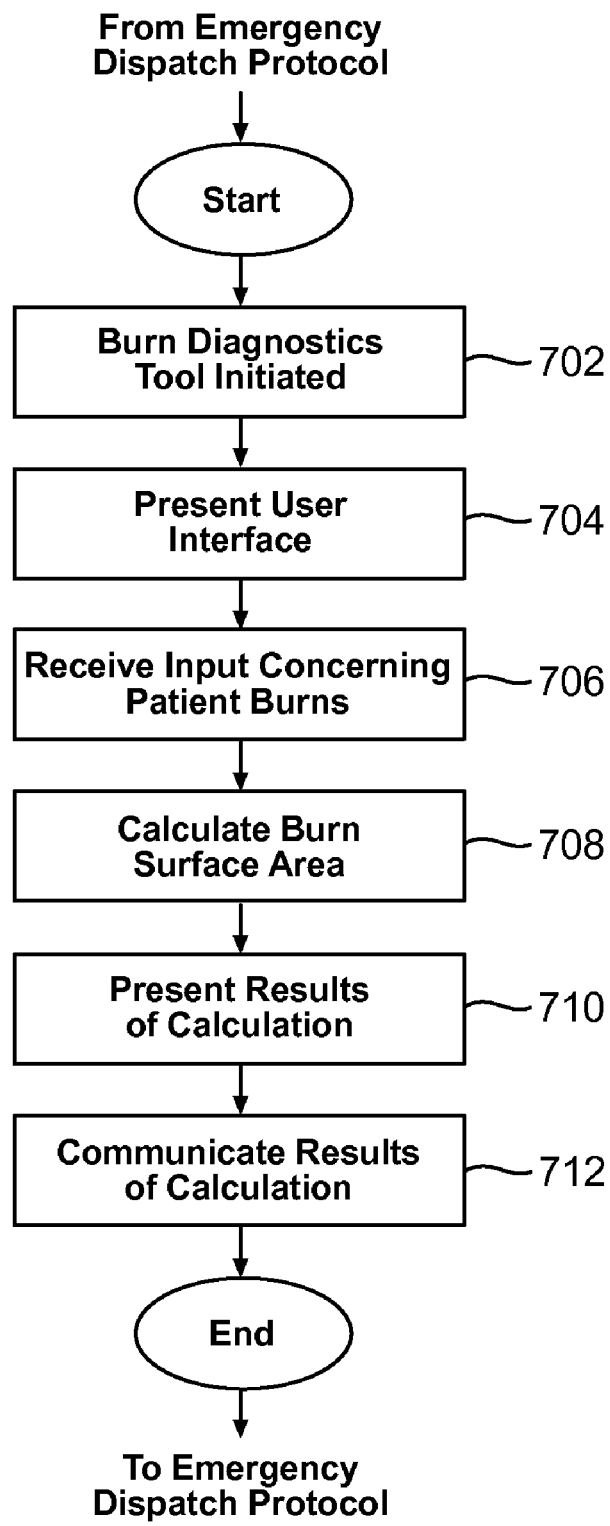
FIG. 7 is a flow diagram of a protocol of a burn diagnostic tool, according to one embodiment.

FIG. 7 is a flow diagram of one embodiment of a protocol 700 of a burn diagnostic tool, according to one embodiment. The burn diagnostic tool may be initiated 702 (e.g., launched) from within the emergency dispatch protocol. The emergency dispatch protocol may automatically launch the tool based on input received by the emergency dispatch protocol indicating that the patient may have severe burns. The burn diagnostic tool may also be launched manually, as desired, by the dispatcher.

The burn diagnostic tool may present 704 a user interface comprising a portrayal of a human body divided into a plurality of sections, as previously described. The plurality of sections may comprise inputs to allow a dispatcher to provide input to the tool concerning the burned areas of a patient's body. Accordingly, the diagnostic tool may receive 706 input corresponding to the plurality of sections of the portray of the human body and indicating the burned areas of the patient's body.

Upon receiving 706 input indicating one or more burned areas of the patient's body, the burn diagnostic tool may calculate 708 the burn surface area based on the received input. The burn diagnostic tool may present 710 the results of the calculation. The burn diagnostic tool may also communicate 712 the results of the calculation to another system such as the emergency dispatch protocol. At any time the burn diagnostic tool may be terminated and control may be transferred from the burn diagnostic tool back to the emergency dispatch protocol.

The embodiments described above, as previously mentioned, may transfer or otherwise communicate the burn surface calculation to the emergency medical dispatch protocol and/or the determinant value calculator to aid in determining the priority of the dispatch response. The result of the burn surface calculation may be incorporated into the traversal of the logic tree of the emergency dispatch protocol. For example, subsequent determinations as to how the emergency dispatch protocol proceeds along the logic tree may be based, at least in part, upon the burn surface calculation of the burn diagnostic tool. A person of ordinary skill can appreciate that the burn surface calculation and/or input to the burn diagnostic tool may be communicated to other components of the emergency medical dispatch system 100 as well. Moreover, other information may be communicated as well. All information gathered by the diagnostic tools may be stored by the system 100 and conveyed to the determinant value calculator 110, the reporting module 114, the CAD system 112, and/or to trained emergency responders. This information may be used to assist emergency responders prior to arrival. The diagnostic tools 120, including the burn diagnostic tool 122, greatly improve information collection and intervention for emergency medical response situations and will be an aid in saving lives.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed is:

1. A computer-implemented method to assist a dispatcher when communicating with a caller via telephone regarding a medical emergency of a patient, comprising:
    a dispatch center computer system providing an emergency dispatch protocol to assist the dispatcher, the protocol presenting a plurality of pre-scripted interrogatories for the dispatcher to ask the caller to gather information regarding the emergency and generate an emergency dispatch response by emergency responders;
    the dispatch center computer system initiating a diagnostic tool on the dispatch center computer, the diagnostic tool configured to assist the dispatcher in determining a burn surface area on the patient; and
    the diagnostic tool presenting to the dispatcher a user interface comprising a portrayal of a human body divided into a plurality of sections to enable a dispatcher to quickly sum a surface area of each of the sections that correspond to burned areas of the patient's body to determine the burn surface area of the patient.

2. The computer-implemented method of claim 1, wherein the surface area of each of the plurality of sections includes an indication of an approximate percentage of the total surface area of the portrayed human body.

3. The computer-implemented method of claim 1, wherein the plurality of sections represent a multiple of nine percent of the total surface area of the portrayed human body.

4. The computer-implemented method of claim 1, wherein the plurality of sections of the human body portrayed on the user interface include: face, back of head, chest and abdomen, back, front of right arm, front of left arm, back of right arm, back of left arm, front of right leg, front of left leg, back of right leg, and back of left leg.

5. The computer-implemented method of claim 4, wherein the plurality of sections of the human body portrayed on the user interface further include: genitalia, front of neck, and back of neck.

6. The computer-implemented method of claim 1, wherein the plurality of sections comprise at least eleven sections, each section representing approximately nine percent of the total surface area of the portrayed human body.

7. The computer-implemented method of claim 6, wherein the eleven sections of the human body portrayed on the user interface are: head, right arm, left arm, chest, abdomen, upper back, lower back, front of right leg, front of left leg, back of right leg, and back of left leg.

8. The computer-implemented method of claim 6, wherein the eleven sections of the human body portrayed on the user interface are: head, right arm, left arm, chest, abdomen, upper back, lower back, right thigh, left thigh, right leg (below the knee), and left leg (below the knee).

9. The computer-implemented method of claim 1, further comprising the diagnostic tool receiving dispatcher-entered input indicative of caller-relayed information concerning the caller's observations of the burned areas of the patient's body, wherein the caller's observations are vocally relayed over the telephone to the dispatcher.

10. The computer-implemented method of claim 9, wherein the dispatcher-entered input corresponds to one or more of the plurality of sections of the body.

11. The computer-implemented method of claim 9, further comprising the diagnostic tool calculating the burn surface area on the patient's body based on the received dispatcher-entered input indicative of the caller relayed information.

12. The computer-implemented method of claim 11, further comprising the diagnostic tool communicating to the emergency dispatch protocol the results of the calculation of the burn surface area of the patient.

13. The computer-implemented method of claim 12, further comprising the dispatch center computer system determining a priority for the emergency medical dispatch response based on the results of the diagnostic tool calculation of the burn surface area of the patient.

14. The computer-implemented method of claim 13, wherein the dispatch center computer system determining the priority further comprises determining a determinant value.

15. The computer-implemented method of claim 11, wherein the diagnostic tool calculating the burn surface area comprises estimating the percentage of the patient's body that is burned.

16. The computer-implemented method of claim 1, further comprising the dispatch center computer system communicating to the diagnostic tool information relating to the age of the patient gathered by the emergency dispatch protocol, and wherein the portrayal of the human body presented by the diagnostic tool user interface is one of a portrayal of an infant, a portrayal of a child, and a portrayal of an adult, based on the age of the patient.

17. The computer-implemented method of claim 1, wherein the dispatch center computer system initiates the diagnostic tool based on dispatcher-entered input indicative of one or more responses of the caller to the interrogatories presented to the dispatcher by the protocol.

18. The computer-implemented method of claim 1, further comprising the dispatch center computer system presenting to the dispatcher an emergency dispatch protocol user interface having a diagnostic tool launch input to initiate the diagnostic tool, wherein the dispatch center computer system initiates the diagnostic tool in response to the diagnostic tool launch input.

19. A computer-implemented method to assist a dispatcher when communicating with a caller via telephone regarding a medical emergency of a patient, comprising:
    a dispatch center computer system providing an emergency dispatch protocol to assist the dispatcher, the protocol presenting a plurality of pre-scripted interrogatories for the dispatcher to ask the caller to gather information regarding the emergency and generate an emergency dispatch response by emergency responders;
    the dispatch center computer system initiating a diagnostic tool on the dispatch center computer, the diagnostic tool configured to assist the dispatcher in determining a burn surface area on the patient;
    the diagnostic tool presenting to the dispatcher a user interface;
    the diagnostic tool receiving dispatcher-entered input indicative of caller relayed information concerning the caller's observations of the burned areas of the patient's body, wherein the caller's observations are vocally relayed over the telephone to the dispatcher;

the diagnostic tool calculating a burn surface area on the patient's body based on the dispatcher-entered input indicative of the caller relayed information; and the diagnostic tool providing the results of the calculation of the burn surface area of the patient.

20. The computer-implemented method of claim 19, wherein the diagnostic tool user interface comprises a portrayal of a human body divided into a plurality of sections, and wherein the dispatcher-entered input corresponds to the plurality of sections.

21. The computer-implemented method of claim 19, wherein the diagnostic tool providing the results of the calculation of the burn surface area of the patient comprises the diagnostic tool displaying the results of the calculation via the user interface.

22. The computer-implemented method of claim 19, wherein the diagnostic tool providing the results of the calculation of the burn surface area of the patient comprises the diagnostic tool communicating the results of the calculation to the emergency dispatch protocol.

23. The computer-implemented method of claim 19, further comprising the dispatch center computer system presenting to the dispatcher an emergency dispatch protocol user interface having a diagnostic tool launch input to initiate the diagnostic tool, wherein the dispatch center computer system initiates the diagnostic tool in response to the diagnostic tool launch input.

24. The computer-implemented method of claim 19, further comprising the diagnostic tool providing input fields via the user interface, wherein the input fields are associated with sections of the portrayal of the human body such that the dispatcher can enter input indicative of which sections of the patient's body are burned.

25. The computer-implemented method of claim 24, wherein the input fields comprise clickable areas on the sections of the portrayal of the human body of the diagnostic tool user interface, such that a dispatcher can click on a clickable area of a section of the portrayal of the human body to indicate to the diagnostic tool that the corresponding section of the patient's body is burned.

26. A computer-readable storage medium including computer-readable instruction code for performing a method to assist a dispatcher when communicating with a caller via telephone regarding a medical emergency of a patient, the method comprising:

a dispatch center computer system providing an emergency dispatch protocol to assist the dispatcher, the protocol presenting a plurality of pre-scripted interrogatories for the dispatcher to ask the caller to gather information regarding the emergency and generate an emergency dispatch response by emergency responders;

the dispatch center computer system initiating a diagnostic tool on the dispatch center computer, the diagnostic tool configured to assist the dispatcher in determining a burn surface area on the patient; and the diagnostic tool presenting to the dispatcher a user interface comprising a portrayal of a human body divided into a plurality of sections to enable a dispatcher to quickly sum a surface area of each of the sections that correspond to burned areas of the patient's body to determine the burn surface area of the patient.

27. A computer system to perform a method to assist a dispatcher when communicating with a caller via telephone regarding a medical emergency of a patient, the computer system comprising:

a processor;

an input device in electrical communication with the processor;

an output device in electrical communication with the processor; and a memory in electrical communication with the processor, and having stored thereon:

an emergency dispatch protocol including a plurality of pre-scripted interrogatories for a dispatcher to ask a caller to generate an emergency dispatch response; and a diagnostic tool to assist the dispatcher in determining the burn surface area of the patient, wherein the diagnostic tool is configured to present to the dispatcher a user interface comprising a portrayal of a human body divided into a plurality of sections.

28. The computer system of claim 27, wherein the diagnostic tool is further configured to calculate the burn surface area of the patient based on input provided by the dispatcher to the diagnostic tool via the user interface.

29. The computer system of claim 27, wherein the diagnostic tool is further configured to provide to the emergency dispatch protocol the burn surface area of the patient.

30. The computer system of claim 27, further comprising a determinant value calculator stored on the memory to calculate a determinant value to prioritize an emergency response, wherein the diagnostic tool is configured to provide to the determinant value calculator the burn surface area of the patient.

31. The computer system of claim 27, further comprising a reporting module stored on the memory to measure the performance of a dispatcher, wherein the diagnostic tool is configured to provide to the reporting module the burn surface area of the patient.

* * * * *